(12) United States Patent
Lee et al.

(10) Patent No.: US 7,516,022 B2
(45) Date of Patent: Apr. 7, 2009

(54) METHOD AND SYSTEM FOR ASSESSING QUALITY OF SPOT WELDS

(75) Inventors: Hsu-Tung Lee, Surrey (CA); Roman Gr. Maev, Windsor (CA); Elena Yu Maeva, Windsor (CA); Serguei A Titov, Moscow (RU)

(73) Assignee: Chrysler LLC, Auburn Hills, MI (US)

( * ) Notice: Subject to any disclaimer, the term of this patent is extended or adjusted under 35 U.S.C. 154(b) by 0 days.

(21) Appl. No.: 11/536,726

(22) Filed: Sep. 29, 2006

(65) Prior Publication Data
US 2007/0038400 A1    Feb. 15, 2007

Related U.S. Application Data

(62) Division of application No. 10/370,540, filed on Feb. 20, 2003, now Pat. No. 7,132,617.

(60) Provisional application No. 60/359,280, filed on Feb. 20, 2002, provisional application No. 60/359,275, filed on Feb. 20, 2002.

(51) Int. Cl.
*G06F 17/40* (2006.01)
*G06F 19/00* (2006.01)
*G01B 17/00* (2006.01)
*G01B 21/32* (2006.01)

(52) U.S. Cl. ............................. 702/39; 73/588; 73/596; 73/597; 73/598; 73/600; 73/602; 73/627; 73/866; 702/33; 702/34; 702/35; 702/187; 702/189

(58) Field of Classification Search ................... 702/39, 702/1, 33, 34, 35, 108, 113, 127, 187, 189; 73/570, 579, 581, 588, 592, 596, 597, 598, 73/599, 600, 602, 627, 628, 632, 865.9, 866; 340/500, 540
See application file for complete search history.

(56) References Cited

U.S. PATENT DOCUMENTS 3,038,329 A * 6/1962 Miller ........................ 73/588
(Continued)

FOREIGN PATENT DOCUMENTS

GB        715143        3/1953
(Continued)

OTHER PUBLICATIONS

Schmid, Rudi, "Ultrasonic Testing of Austenitic and Dissimilar Metal Welds," Dec. 1997, NDTnet, vol. 2, No. 12, 4.7.1.*

*Primary Examiner*—Edward R Cosimano
(74) *Attorney, Agent, or Firm*—Ralph E. Smith

(57) ABSTRACT

A system and method for assessing the quality of spot weld joints between pieces of metal includes an ultrasound transducer probing a spot weld joint. The ultrasound transducer transmits ultrasonic radiation into the spot weld joint, receives corresponding echoes, and transforms the echoes into electrical signals. An image reconstructor connected to the ultrasound transducer transforms the electrical signals into numerical data representing an ultrasound image. A neural network connected to the image reconstructor analyzes the numerical data and an output system presents information representing the quality of the spot weld joint. The system is trained to assess the quality of spot weld joints by scanning a spot weld joint with an ultrasound transducer to produce the data set representing the joint; then physically deconstructing the joint to assess the joint quality.

6 Claims, 17 Drawing Sheets

U.S. PATENT DOCUMENTS

| | | | |
|---|---|---|---|
| 3,384,733 A | 5/1968 | Burbank et al. | |
| 3,410,983 A | 11/1968 | Deutsch | |
| 3,726,130 A | 4/1973 | Hurlebaus | |
| 3,810,385 A | 5/1974 | McFaul et al. | |
| 4,099,045 A | 7/1978 | Okuda et al. | |
| 4,208,917 A | 6/1980 | Aoyama et al. | |
| 4,449,029 A | 5/1984 | Nied | |
| 4,472,620 A | 9/1984 | Nied | |
| 4,530,362 A | 7/1985 | Hetz | |
| 4,596,143 A | 6/1986 | Norel | |
| 4,658,827 A * | 4/1987 | He et al. | 600/442 |
| 5,155,439 A * | 10/1992 | Holmbo et al. | 324/534 |
| 5,280,724 A | 1/1994 | Higo et al. | |
| 5,306,893 A | 4/1994 | Morris et al. | |
| 5,383,366 A | 1/1995 | Wallingford et al. | |
| 5,448,503 A | 9/1995 | Morris et al. | |
| 5,450,315 A | 9/1995 | Stefanski | |
| 5,486,734 A * | 1/1996 | Seyed-Bolorforosh | 310/327 |
| 5,644,085 A | 7/1997 | Lorraine et al. | |
| 5,659,479 A | 8/1997 | Duley et al. | |
| 5,674,415 A | 10/1997 | Leong et al. | |
| 5,677,490 A | 10/1997 | Gunther et al. | |
| 5,764,859 A | 6/1998 | Kim et al. | |
| 5,774,376 A | 6/1998 | Manning | |
| 5,814,731 A | 9/1998 | Alexander et al. | |
| 6,018,729 A | 1/2000 | Zacharia et al. | |
| 6,198,071 B1 | 3/2001 | Kitsunai | |
| 6,297,467 B1 * | 10/2001 | Maev et al. | 219/109 |
| 6,546,803 B1 * | 4/2003 | Ptchelintsev et al. | 73/632 |
| 6,798,715 B2 * | 9/2004 | Harmon et al. | 367/99 |
| 7,132,617 B2 * | 11/2006 | Lee et al. | 219/109 |
| 2002/0008086 A1 | 1/2002 | Fujii et al. | |
| 2003/0234239 A1 * | 12/2003 | Lee et al. | 219/109 |
| 2004/0245315 A1 * | 12/2004 | Maev et al. | 228/8 |
| 2005/0230360 A1 * | 10/2005 | Maev et al. | 219/109 |

FOREIGN PATENT DOCUMENTS

| | | |
|---|---|---|
| GB | 774675 | 12/1953 |
| GB | 2 015 159 A | 2/1979 |

* cited by examiner

|  | binary filter | gray - level filter |
|---|---|---|
| DILATION | Increase the geometrical area of an object by setting the background area pixel, which is adjacent to the object, to the same gray-level as that of the object. | Smooth small negative gray-level regions. |
|  | $A \oplus B = \{t \in Z^2 : t = a+b, a \in A, b \in B\}$ | $A \oplus B = max[A(x+i, y+j) + B(i,j)]$ |
| EROSION | Reduce the geometrical area of an object by setting the pixels at contour region to the gray - level of their background value. | Smooth small positive gray - level regions. |
|  | $A \ominus B = (A^c + B^c)$ | $A \ominus B = min[A(x+i, y+j) - B(i,j)]$ |

Where  $\oplus$  is the operator for dilation,
$\ominus$  is the operator for erosion,
A   is an object inside an image, and a is a pixel in A,
B   is a structural function or mask, and b is a member in a structural function, and
x, y  are coordinators defined in A and B.
These two operations offer tools to study the combined effects of porous inclusion where multiple defects exist in a small region.

*Figure - 8*

|  | Group one | Group two | Group three |
|---|---|---|---|
| Microscope(s) used | SPSAM | SPSAM | Hand-held device and SPSam |
| Experiment procedure 1 | Nondestructive only | Destructive and nondestructive | Destructive and nondestructive |
| Experiment procedure 2 | Identified by expert for their quality (setup / nominal / minimum / less than minimum / stick) | Perform peel tests and measure the nugget diameters | Perform peel tests and measure the nugget diameters |
| Current status | Serve as the calibration coupon for nondestructive testing in industries | destroyed | destroyed |
| Result of collected data | Acoustic images and quality information (good/bad weld) | Acoustic images and quantity information (weld diameter) | Acoustic images and quantity information (weld diameter) |
| Number of specimens | 390 | 13 | 46 |

*Figure - 11*

|  | Type I | Type II |
|---|---|---|
| Setup | 5.1 ± 0.4 mm | 6.4 ± 0.4 mm |
| Nominal | 4.4 ± 0.4 | 5.6 ± 0.4 |
| Minimum | 3.6 + 0.4 | 4.8 + 0.4 |
| Less than minimum | 1.8 ± 0.4 | 2.4 ± 0.4 |
| Stick | No nugget | No nugget |

*Figure - 12*

| TYPE I Stack up | Result of image analysis ||| Experts' result ||
|---|---|---|---|---|---|
|  | Area | Max. diameter | Min. diameter | Nugget diameter | Quality |
|  | 14.0 | 4.5 | 3.3 | 1.9 | Less than min. |
|  | 15.0 | 5.3 | 2.8 | 1.4 | Less than min. |
|  | 18.0 | 5.7 | 3.0 | 2.1 | Less than min. |
|  | 12.0 | 5.0 | 2.5 | 1.9 | Less than min. |
|  | 16.0 | 5.0 | 2.5 | 2.1 | Less than min. |
|  | 14.0 | 5.2 | 2.5 | 1.9 | Less than min. |
|  | 11.0 | 5.0 | 2.5 | 1.7 | Less than min. |
|  | 12.0 | 4.9 | 2.5 | 1.5 | Less than min. |
|  | 16.0 | 5.3 | 2.5 | 1.7 | Less than min. |
|  | 14.0 | 5.1 | 2.5 | 1.5 | Less than min. |
|  | 14.0 | 4.9 | 2.5 | 2.0 | Less than min. |
|  | 15.0 | 5.3 | 3.5 | 1.8 | Less than min. |
|  | 14.0 | 5.1 | 3.3 | 1.8 | Less than min. |

*Figure - 13*

|  | area | maximum axis | minimum axis | output | peel test diameter | weld quality | result |
|---|---|---|---|---|---|---|---|
| weld 78 | 31.0 | 6.7 | 5.5 | good | 5.65 | setup | match |
| weld 81 | 42.0 | 7.3 | 6.3 | good | 5.5 | setup | match |
| weld 82 | 38.0 | 7.6 | 6.0 | good | 5.5 | setup | match |
| weld 86 | 24.0 | 6.0 | 4.5 | good | 5.5 | setup | match |
| weld 88 | 22.0 | 5.8 | 4.3 | good | 4.45 | nominal | match |
| weld 90 | 21.0 | 5.9 | 4.0 | good | 4.0 | minimum | match |
| weld 92 | 21.0 | 5.7 | 4.3 | good | 3.65 | minimum | match |
| weld 94 | 19.0 | 5.6 | 4.0 | bad | 3.5 | less than | match |
| weld 96 | 19.0 | 5.7 | 3.8 | bad | 2.24 | less than | match |
| weld 98 | 17.0 | 5.6 | 3.8 | bad | 2.2 | less than | match |
| weld 100 | 15.0 | 5.2 | 3.8 | bad | 0 | stick | match |
| weld 102 | 14.0 | 5.2 | 3.8 | bad | 0 | stick | match |
| weld 104 | 0.0 | 0.0 | 0.0 | bad | 0 | stick | match |

*Figure - 17*

| Sample number | Peel test diameter | Acoustic parameters | | |
|---|---|---|---|---|
| | | Diameter (mm) | inclusion area | indentation |
| #1 | 0 | 2 | 0 | 5 |
| #1_opp | 0 | 1.77 | 0.45 | 3 |
| #3 | 0 | 3.85 | 3.3 | 5 |
| #3_opp | 0 | 4.2 | 5.6 | 3 |
| #6 | 2.13 | 5.18 | 1.8 | 10 |
| #6_opp | 2.13 | 5.3 | 2.6 | 7 |
| #9 | 3.27 | 5.52 | 1.9 | 12 |
| #9_opp | 3.27 | 5.41 | 2.15 | 10 |
| #10 | 3.57 | 6.06 | 0.8 | 20 |
| #10_opp | 3.57 | 5.7 | 0.55 | 15 |
| #12 | 4.15 | 5.83 | 0 | 22 |
| #12_opp | 4.15 | 5.7 | 0 | 18 |
| #14 | 4.65 | 5.9 | 0 | 32 |
| #14_opp | 4.65 | 5.85 | 0 | 27 |
| #16 | 5.2 | 6.47 | 0 | 40 |
| #16_opp | 5.2 | 6.41 | 0 | 34 |
| #17 | 5.3 | 6.57 | 0 | 50 |
| #17_opp | 5.3 | 6.63 | 0 | 40 |
| #19 | 6.05 | 6.74 | 0 | 50 |
| #19_opp | 6.05 | 6.52 | 0 | 45 |
| #23 | 6.55 | 7.59 | 0 | 55 |
| #23_opp | 6.55 | 7.06 | 0 | 60 |
| #26 | 6.45 | 6.64 | 0 | 65 |
| #26_opp | 6.45 | 6.46 | 0 | 50 |
| #27 | 6.4 | 6.8 | 0 | 60 |
| #27_op | 6.4 | 6.85 | 0 | 55 |
| #57 | 3 | 6.16 | 2.45 | 6 |
| #57_opp | 3 | 5.7 | 9 | 11 |
| #59 | 4.2 | 6.5 | 3.5 | 6 |
| #59_opp | 4.2 | 6.5 | 9.75 | 11 |
| #61 | 5.3 | 6.71 | 3.6 | 8 |
| #61_opp | 5.3 | 6.65 | 1.85 | 13 |
| #66 | 5.4 | 6.6 | 1.7 | 8 |
| #66_opp | 5.4 | 6.77 | 1.15 | 15 |
| #67 | 5.5 | 6.64 | 0 | 8 |
| #67_opp | 5.5 | 6.75 | 0 | 14 |
| #68 | 5.58 | 6.51 | 0 | 9 |
| #68_opp | 5.58 | 6.8 | 0 | 15 |
| #70 | 5.95 | 6.63 | 0 | 8 |
| #70_op | 5.95 | 6.85 | 0 | 20 |
| #72 | 7.2 | 7.8 | 0 | 40 |
| #72_op | 7.2 | 7.87 | 0 | 50 |
| #73 | 7.3 | 7.84 | 0 | 30 |
| #73_op | 7.3 | 7.8 | 0 | 50 |
| #74 | 7.4 | 7.68 | 0 | 30 |
| #74_op | 7.4 | 7.96 | 0 | 60 |

*Figure - 18*

| Linear model | | | | | | | | | |
|---|---|---|---|---|---|---|---|---|---|
| $C_0$ | $C_1$ | $C_2$ | $C_3$ | | | | | | |
| -3.340 | 0.0154 | 0.0791 | 0.0433 | | | | | | |
| Nonlinear model | | | | | | | | | |
| $C_0$ | $C_1$ | $C_2$ | $C_3$ | $C_4$ | $C_5$ | $C_6$ | $C_7$ | $C_8$ | $C_9$ |
| 0.3962 | 0.2333 | -1.050 | -0.255 | 0.0008 | 0.2826 | 0.0201 | -0.041 | -0.029 | 0.0139 |

*Figure - 20*

| Nonlinear model (after parameter screening) | | | | | | |
|---|---|---|---|---|---|---|
| $C_0$ | $C_1$ | $C_2$ | $C_3$ | $C_4$ | $C_5$ | $C_6$ |
| 0.93835 | 0.31894 | -1.66622 | 0.00044 | 0.34996 | -0.00739 | -0.04926 |

*Figure - 21*

METHOD AND SYSTEM FOR ASSESSING QUALITY OF SPOT WELDS

CROSS-REFERENCE TO RELATED APPLICATIONS

This application is a Divisional of U.S. patent application Ser. No. 10/370,540, filed Feb. 20, 2003 now U.S. Pat. No. 7,132,617, which claims the benefit of U.S. Provisional Patent Application Ser. No. 60/359,280 filed Feb. 20, 2002, now expired, and U.S. Provisional Patent Application Ser. No. 60/359,275, filed Feb. 20, 2002, now expired.

FIELD OF THE INVENTION

The present invention relates generally to a method and system for assessing the quality of spot welds and, more particularly, a non-destructive method and system for assessing the quality of spot welds according to measured acoustic parameters.

BACKGROUND OF THE INVENTION

Sheet metal joining processes are widely used in many industries, such as the aerospace and automotive industries. Among these processes, resistance spot welding is the most common procedure used to join metal sheets because it has high process speed and is easily adopted in mass production lines. As these industries grow, the quality control of spot welds becomes an important issue for manufacturers eager to improve their output capacity and product quality.

The quality of the spot weld is affected by welding processes and the design of the joint. Many factors have to be taken into account, such as metallurgic reactions, thermal behaviors, chemical composition, condition of the base metal, welding conditions, and the welding equipment. Furthermore, the intricate relationship between these factors makes it more difficult to control the quality of spot welds. Numerous efforts have been made to improve weld quality through different approaches, nevertheless, most of them are not overall solutions due to the lack of adequate equipment and efficient algorithms to inspect these improvements.

The conventional strategy for spot weld quality control inspection usually consists of a weld current-resistance monitoring system to maintain consistent welding parameters, and an after weld, spot weld examination process, according to a standard set up by the American Welding Society for a particular industry. The spot weld examination standard typically includes visual inspection of the weld surface and destructive testing of collected weldment. To determine weld quality, visual inspection of the surface appearance and weld size are important indicators. Other important indicators, by destructive inspection, are weld size, penetration, strength, ductility, internal discontinuities, and sheet separation and expulsion. Weld consistency, assessed by monitoring welding parameters, is another important indicator. But these weld quality indicators are vague due to the insufficient quantified description. To apply these specifications in practical manufacturing cases, the indicators must be converted to quantified inspection standards. The Welding Handbook and the Resistance Welding Manual do indeed quantify these indicators, but even then spot weld quality control relies mainly on an on-line supervising unit to monitor welding parameters, on-line inspectors to perform visual inspection, and statistical sampling techniques for off-line destructive testing.

More importantly, the weld quality indicators are mostly for visual inspection and destructive testing, which are typically separately conducted. Thus, present weld quality control does not take into account the combined effect of those indicators. Furthermore, the true quality of the spot weld, i.e., its strength, is only presumed by off-line destructive sample tests. Unless every spot weld is examined, there is no certainty that the required strength has been met.

Acoustic methods are a commonly used non-destructive testing method that has been used for various inspection applications. Unlike other non-destructive testing methods, the acoustic method provides both surface and internal information. Moreover, the acoustic method allows deeper penetration into specimens and higher sensitivity to small discontinuities. Acoustic methods, however, are not flawless. The most significant limitations include the requirements of a propagating medium, or couplant fluid, which is required for acoustic wave propagation between the acoustic probe and the test specimen, and skillful operators for operating the devices and analyzing the acoustic information.

While the first limitation is typically overcome because the materials for joining in the automotive and aerospace industries are usually galvanized or coated and thus will not be damaged by any couplant fluid, the second limitation—the need for skillful operators—is much more significant. The on-line inspection of spot welds is very difficult because it is not economical to train every worker in the plant to be a tester/analyzer/operator.

More importantly, the acoustic method, by its very nature, limits the practicality of an on-line inspection. The acoustic method, unlike the optical or x-ray method that receives two-dimensional information through one process, has to go through point-to-point scanning procedures to obtain two-dimensional information. There are several ways to display acoustic information, and they can be categorized by the information obtained. The most common ones are A-, B-, and C-scans that can be selected to show the internal defects as required.

The A-scan, the simplest presentation, and widely used is conventional ultrasonic NDE devices, shows the amplitude of the echoes, or the reflection, as a function of time at a selected point on the work surface. The duration of time between different peaks represents the time needed for acoustic waves to travel between discontinuities.

The B-scan follows the same procedure as the A-scan, but repeats the signal-catching procedures while the probe scans along the straight line on the surface. Thus, an image of the cross-section of a component is built up. The measured amplitude is displayed as a colored dot on the monitor and its coordinant is defined by the position of the probe (X-coordinate) and the traveling time (Y-coordinate) of the acoustic pulse.

If the amplitude of a particular echo is monitored at each point on a certain depth of the workpiece, a C-scan can be performed. Measurements at each point are taken using two-dimensional scanning and electronic gate mechanisms that produce the plan for the level of the defect. This scan only gives the information at the preset depth of the electronic gate. While the C-scan provides the richest information, and is therefore more desirable for quality control purposes, it is also the most time consuming scan, and therefore difficult to perform on-line.

Conventional quality control devices for spot welding cannot perform on-line inspection of spot welds, nor can they provide feedback to the welding control system. In this way, the traditional quality control systems are similar to statistical welding parameter monitoring systems. While it is imperative to combine the idea of on-line quality inspection with closed-loop feedback control in a robust spot-welding control system, there is not an acoustic method capable of manipulating real-time control and on-line quality inspection.

SUMMARY OF THE INVENTION

A novel acoustic method and system provides real-time scanning for on-line quality inspection of spot welds. The method and system allows a large amount of acoustic information to be retrieved, processed, and presented in a short period of time to facilitate on-line, non-destructive inspection of spot welds employing intelligent control software and state-of-the-art hardware. This intelligent system for on-line, real-time, non-destructive inspection of spot welds employs novel algorithms for analyzing the information acquired by an acoustic device, and is capable of providing go/no-go responses to on-line workers in a real-time fashion. Furthermore, feedback can be provided to the welding control unit during the inspection process.

The method and system for spot weld quality assessment correlates the quality of spot welds with acoustical parameters built by statistical and neural network methods. The statistical and neural network methods provide precise predictions for assessing weld quality and allow the on-line inspection of spot weld quality in real time. The method and apparatus for acoustic inspection detects any inconsistent weld strength, and provides feedback to the welding unit, whereby designers are able to reduce the total number of spot welds and reduce manufacturing costs.

The invention overcomes the limitations of the acoustic imaging and provides a closed-loop feedback quality-advisor method and system. Once the acoustic inspection system detects defects or inconsistent weld strength, the system provides more accurate feedback to the welding unit than traditional current/resistance monitoring. Further, the system and method according to the invention are able to provide on-line feedback of the weld quality and to perform inspections based on the internal structure of the welds, both features that the traditional current/resistance monitoring system were not able to provide. Further, the apparatus and method according to the invention compliment the design process because the integrity of any given weld can be predicted based on the acoustic information, which helps designers reduce the total number of spot welds and thereby reduces the manufacturing costs.

Further areas of applicability of the present invention will become apparent from the detailed description provided hereinafter. It should be understood however that the detailed description and specific examples, while indicating preferred embodiments of the invention, are intended for purposes of illustration only, because various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings, wherein:

FIG. 8 is a table including the mathematical representations of dilation and erosion in accordance with a preferred embodiment of the present invention;

FIG. 11 is a table including weld quality criteria in accordance with a preferred embodiment of the present invention;

FIGS. 12 and 13 are tables summarizing exemplary experimental results in accordance with a preferred embodiment of the present invention;

FIGS. 17 and 18 are tables summarizing exemplary experimental results in accordance with a preferred embodiment of the present invention;

FIGS. 20 and 21 are tables including coefficients of linear and nonlinear models in accordance with a preferred embodiment of the present invention.

DETAILED DESCRIPTION OF THE PREFERRED EMBODIMENTS

Figure 1:
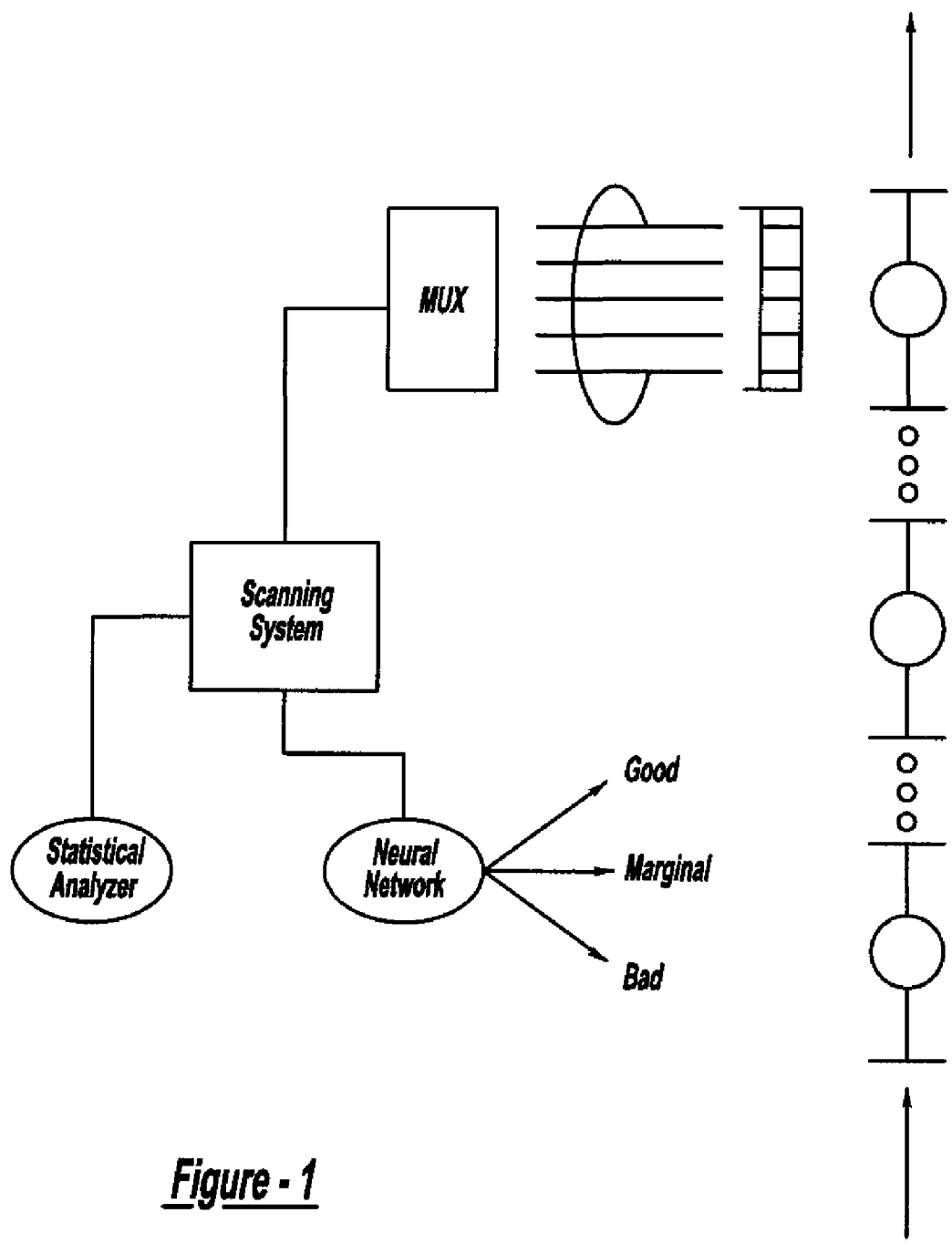
FIG. 1 is a schematic illustrating an acoustic microscope system in accordance with a preferred embodiment of the present invention.

The method and apparatus for assessing the quality of spot welds employs a rapid and robust algorithm for an acoustic or imaging systems. An acoustic microscope system such as one described in U.S. patent application Ser. No. 09/283,397, filed Apr. 1, 1999 now U.S. Pat. No. 6,297,467 and hereby incorporated by reference, is shown schematically in FIG. 1. The software and algorithms according to the invention rapidly analyze the information acquired by the acoustic device, and provide a go/no-go response to on-line workers in a real-time fashion. Optionally, feedback can be provided to a welding control unit during the inspection process.

Acoustic Wave Propagation through a Weld Nugget

Figure 2:
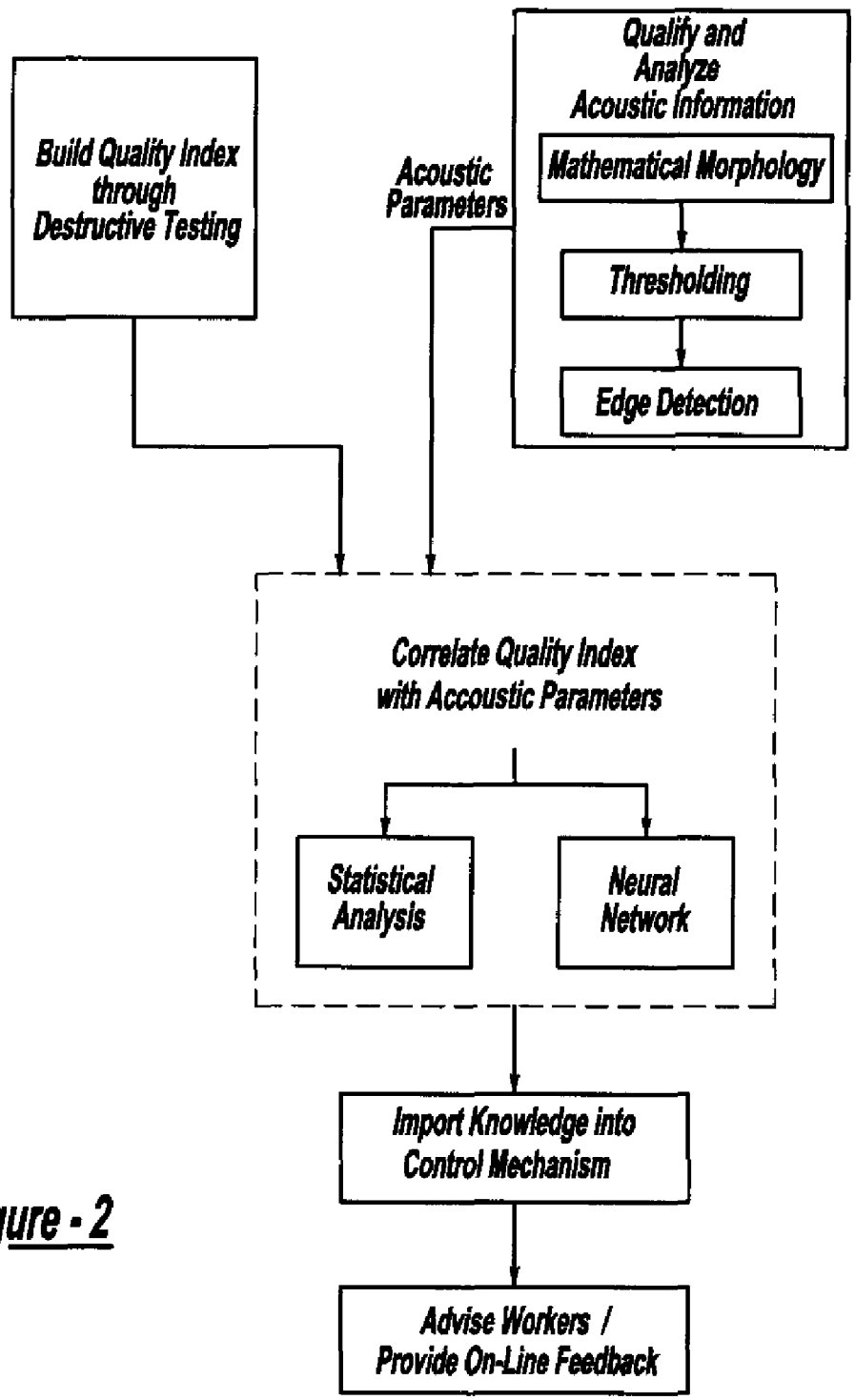
FIG. 2 is a flow chart for a method of analyzing and qualifying spot weld joints in accordance with a preferred embodiment of the present invention.

The spot weld nugget is an anisotropic material with microstructures different from its base metal. With reference to FIG. 2, the study of acoustic wave propagation in the weld nugget includes metallurgical analysis and characterization of the mechanical and physical properties of weld nuggets, including dendrite structures and ferrous areas. Further, the propagation and the interaction of focused acoustic beams inside the spot welds are also analyzed. From this analysis and characterization, the connection between weld nugget structures and the associated acoustic images are understood.

The relationship between the acoustic information in spot welds and the quality of spot welds is learned through the study of the acoustic images, including information such as the profile of surfaces, shape and size of weld nuggets, and size of defects. After quantifying this information, it is formulated as a quality index of spot welds, whereby the acoustic image can be analyzed to extract the desired information. In order to quantify and analyze this information, the following three steps must be performed: First, mathematical morphology is used to improve the acoustic images by eliminating noise, improving geometrical shape, and reshaping important objects inside the spot weld. Such morphology techniques such as dilation and erosion allow porosity to be grouped geometrically and permit the joint effect of group porosity to be studied. Second, segmentation using a thresholding technique to distinguish desirable objects from noise, whereby the most important information is left for analysis. The threshold that separates the peaks on a color/gray level histogram is selected based on knowledge gained from the mathematical morphology. Third, edge detection is used to distinguish discontinuity information inside the nugget from the nugget area, and to build up clear and continuous boundaries for those objects. After edge detection, the boundaries obtained in edge detection are used to calculate the area of the desired information.

Spot weld quality indexes, for correlation with acoustic image parameters, are established through destructive testing. These quality indexes can include the strength of the weld, the nugget size, and a quality judgment based on an expert opinion.

The study of the parameters can be approached as a two step process. First, the parameters are analyzed statistically, such as through an Analysis Of Variance (ANOVA) method. This contributes to the selection of significant parameters to build up the quality index for welds. After the statistical analysis, a mathematical relationship is built between the weld index and the quantified information. Second, the relationship between the weld quality and the screened parameters from the first step are established using artificial neural networks and non-linear regression methods. The artificial neural network method is used to determine the weld index as a non-quantified good/bad judgment, and to establish the relationship between these non-quantified judgments and the quantified weld index information. The non-linear regression method, targeted at simpler weld quality indicators (e.g., the size of welds), is used to build a mathematical relationship between the weld indices obtained in the first step and the quality indicator.

By importing the extracted knowledge into a control mechanism, a portable hand-held acoustic device according to the invention provides an intelligent mechanism for spot weld inspection. The quality evaluation methods provide reliable results, the statistical method provides a nugget diameter predictor, and the neural network model determines nugget integrity. Regardless of which model is adapted, the portable acoustic device serves as an on-line advisor for workers, and provides closed loop feedback to a robot welding control system.

Figure 3:
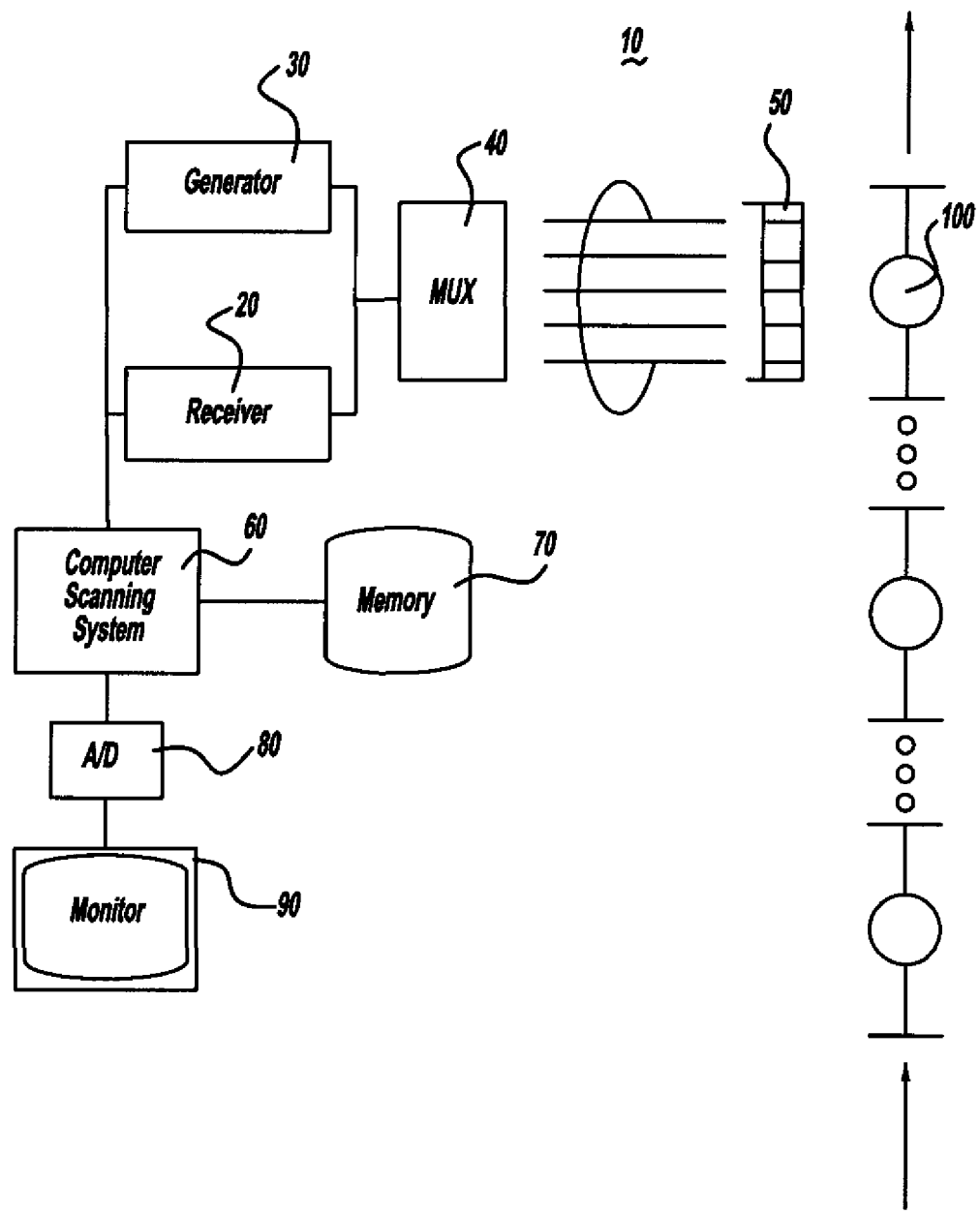
FIG. 3 is a more detailed schematic illustrating an acoustic imaging system in accordance with a preferred embodiment of the present invention.

The method and apparatus according to the invention preferably employs an Acoustic Microscope (AM) 10, which has three-dimensional imaging capability. With reference to FIG. 3, the AM 10 includes an acoustic pulse receiver 20 and generator 30. The pulse generator 30 generates an electrical pulse, and the receiver 20 collects reflected signals. The acoustic wave generated can be a continuous pulse or a short pulse, depending on the system requirements. In the case of matrix array probe, The SAM 10 is connected to an acoustic probe 50 by a multiplexor 40. The acoustic probe 50 includes a planar focus matrix array transducer. Most transducers use a piezomaterial element with an optical quality ground lens to provide the desired quality of acoustic beam alignment and focusing. As a contact with sample used either coupling liquid or polystyrene delay. The material of the acoustic lens should have low attenuation and high velocity to minimize aberrations. The probes are designed for operation with the acoustic beam into various frequencies from 5 MHz to 2 GHz. The transducer converts electric pulses into mechanical vibrations or vice versa.

The precision of the acoustic beam focus primarily depends on spherical aberration; consequently, the spherical aberration itself depends on the ratio of the ultrasound propagation velocities in liquid and the velocities inside the soundguide in the transducer. The AM 10 uses a coupling fluid, which provides the acoustic waves a medium to support their propagation. Between the acoustic probe 50 and a test specimen 100, the medium must be a fluid to allow the scanning procedure. Two major concerns in choosing a couplant fluid are the fluid's attenuation to acoustic waves and its applicability to the test specimen. The performance varies under different coupling fluids and different temperatures. Of all the coupling fluids, water, ultrasound gel and ethanol are the most preferred.

The AM 10 is a computer-controlled ultrasonic scanning system designed for examining the detailed internal structure of a wide range of parts. An AM 10 generally includes: a piezoelectric transducer to generate a high radio frequency acoustical pulse and an acoustic probe, both components included in the acoustic probe 50, with a liquid coupling medium for the pulse to propagate through; an electronic or mechanical scanning system 60 that can relate to the desired region in reliable steps; a memory unit 70 to store the achieved signal step by step; an analog to digital converter 80 to transfer signals to images; and a monitor to display images 90.

The performance of the AM 10 depends on the frequency of the ultrasound wave, type of transducer, the nature of the immersion medium, and the properties of the investigating materials. The nature of the frequency of ultrasound affects the resolution of microscopic imaging and the depth of penetration, but in a contrary way. A higher frequency of ultrasound offers a better resolution microscopic image, but shallower penetration of the testing samples. Thus, to choose a proper frequency of ultrasound for a particular testing example requires a compromise between the resolving power and the degree of penetration.

The microstructure of the nugget region of a spot weld is considered an anisotropic region. In order to assess spot weld quality, it is crucial to formulate the phenomenon of acoustic wave propagation in anisotropic materials. When a weld is deposited, the first grains to solidify are nucleated by the unmelted base metal, and the orientation of crystal grains is in the same direction toward the steepest temperature gradient. While solidifying, metals grow more rapidly in certain crystallographic directions, and the direction of crystal growth is perpendicular to the isotherms. Hence, favorably oriented grains grow faster for substantial distances, while the faster growing grains block the growth of others in a non-favorable orientation. The aforementioned favorable crystallographic direction is the [100] direction in cubic crystals, such as body central cubic or face central cubic. The [100] direction is the least closely packed direction in cubic crystals. The [100] crystals' growth directions and the direction of the steepest temperature gradient are the same in a spot weld because there is no welding speed involved.

Because of the crystals' growth directions, weld pools solidify in a cellular or dendritic growth mode depending on the composition and solidification rates. Both modes cause micro-segregation of alloying elements. As a result, the weld metal may be less homogeneous than the base metal. During the welding solidification, three stages of microstructure formulations can be found. In the first stage, epitaxial growth from the base metal is likely to occur initially in the planar growth front because the temperature differences inside a weld range have an extensive range. In the second stage, during further cooling, the temperature gradient decreases, resulting in a planar to cellular microstructure transition. In the third stage, when the temperature gradient further changes, the primary cellular microstructures become unstable and develop secondary arms called dendritic structure.

$$C_{11} = \lambda$$

Analysis of Wave Propagation in the Nugget of a Spot Weld

Figure 4:
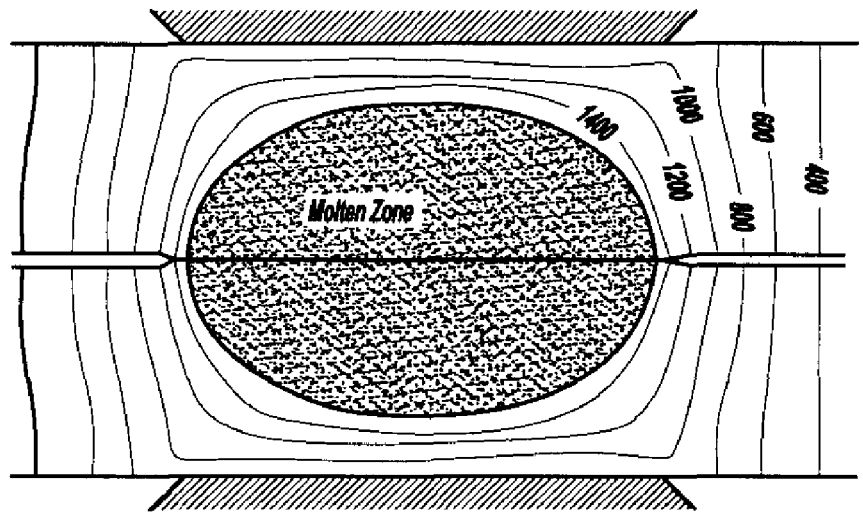
FIG. 4 is a diagram of a theoretical temperature distribution in a spot weld nugget.
Figure 5:
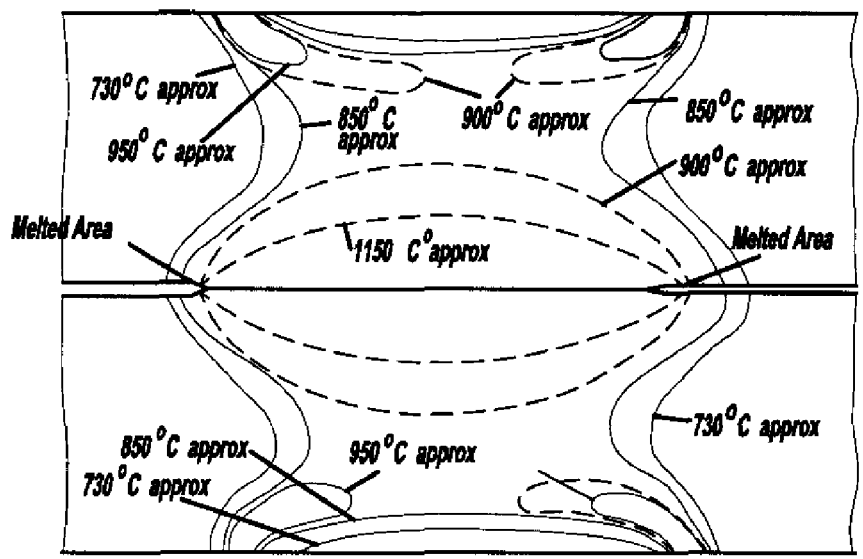
FIG. 5 is a diagram of an experimental temperature distribution in a spot weld nugget.
Figure 6:
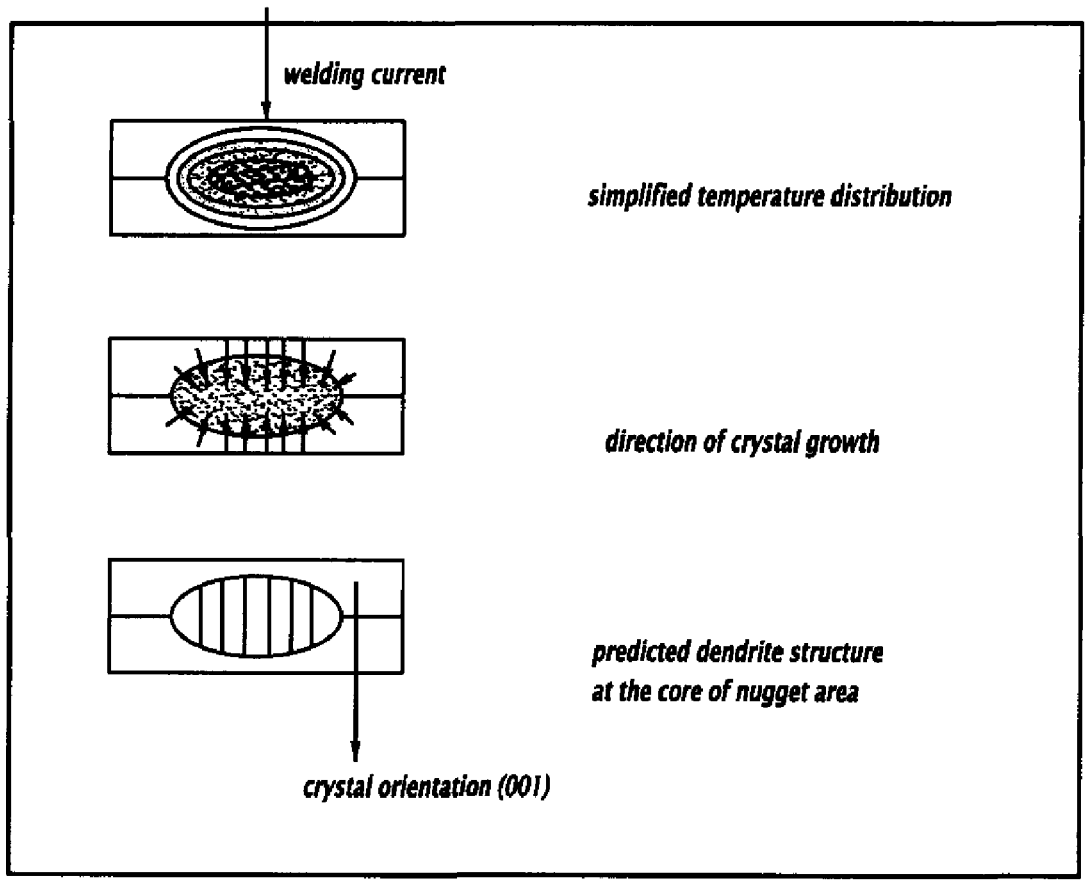
FIG. 6 is a diagram of a nugget structure in a spot weld.

Having reviewed wave propagation in an isotropic material and a primitive anisotropic material, wave propagation in the nugget of a spot weld, which is a hexagonal symmetric case with five elastic constants, will now be described. The spot weld nugget is an irregularly shaped artifact with rough surfaces on both sides, and its metallurgical structure is different from the original sheet metal. Moreover, the existence of discontinuities, porosity, and inclusion inside the weld nugget makes the acoustic wave propagation more difficult to study. The solidification processes in welds affect the crystallographic orientation. The direction of the grain growth follows the steepest temperature gradient, and the crystal growth direction is the [100] direction of the cubic crystal. Thus, for a spot weld, the examining acoustic waves are going through the [100] direction of the dendritic crystals. FIGS. 4 and 5 demonstrate the temperature distribution in both theoretical and experimental analysis. FIG. 6 shows the possible crystal growth direction in the spot weld nugget, which will be on the equiaxed grain.

Because acoustic waves propagate through the [100] direction of the spot weld nugget in the core of the nugget, we can substitute the direction unit into the above equation as l=1, m=0, and n=0. We can derive a simplified wave propagation model as:

$$\lambda_{11} = C_{11}$$

$$\lambda_{22} = \lambda_{33} = C_{44}$$

Solving the eigenvalue problem, then:

$$(C_{11} - \rho C^2)(C_{44} - \rho C^2) = 0$$

The wave speeds are:

$$C_L = \sqrt{\frac{C_{11}}{\rho}} \quad C_{SH} = C_{SV} = \sqrt{\frac{C_{44}}{\rho}}$$

The longitudinal wave speed and the direction calculated here is proven to be correct in Kupperman, D. S., Reimann, K. J., "Ultrasonic Wave Propagation and Anisotropy in Austenitic Stainless Steel Weld Metal", IEEE Transactions on Sonics and Ultrasonics, Vol. SU-27, No. 1, pp. 7-15, 1980, hereby incorporated by reference in its entirety. However, the shear waves traveling across the dendrites region with the polarization direction parallel to the dendrites will have a different attenuation pattern compared to the shear waves propagating in other directions.

The dendrites in spot weld nuggets are long, cylindrical single crystals with orientation in the vertical [100] direction. Assuming the dendrite's cylindrical crystal is symmetric about the Z-axis, as shown in FIG. 6, the general orthorhombic symmetry object can be reduced to be hexagonally symmetrical. The independent elastic constants are reduced from nine (9) to five (5) according to Kupperman and Reimann's study. The five independent elastic constants can be calculated by the modified formula as:

$$\bar{C}_{11D} = \bar{C}_{22D} = \bar{C}_{11} + \frac{3\gamma C}{20}$$

$$\bar{C}_{33D} = \bar{C}_{11} + \frac{2\gamma C}{5}$$

$$\bar{C}_{44D} = \bar{C}_{55D} = \bar{C}_{44} - \frac{\gamma C}{5}$$

$$\bar{C}_{66D} = \bar{C}_{44} + \frac{\gamma C}{20}$$

$$\bar{C}_{13D} = \bar{C}_{23D} = \bar{C}_{12} - \frac{\gamma C}{5}$$

$$\bar{C}_{12D} = \bar{C}_{12} + \frac{\gamma C}{20}$$

where $\lambda$ is the texture anisotropy factor and C can be calculated as: $C = C_{11} - C_{12} - 2C_{44}$. Detailed description can be found in Dewey, B. R., et al, "Measurement of Ansiotropic Elastic Constants of Type 308 Stainless-Steel Electroslag Welds", Experimental Mechanics, Vol. 17, No. 11, pp. 420-26, 1997, and Ekis, J. W., "Ultrasound Examination for Resistance Spot Welds of Filter Connectors", Materials Evaluation, Vol. 52, pp. 462-63, 1994, hereby incorporated by reference in its entirety.

There are two ways to calculate the elastic constants for the spot-weld type of anisotropy. The first one is to use static tensile testing and the second one is to use acoustic testing. According to the first method, samples cut in three principal local directions are fabricated. Tensile tests are then applied at different direction cosines. The longitudinal elongation and the lateral contraction are then measured. Finally, a strain-stress relationship is used to calculate the components of the stiffness matrix.

The second method, the acoustic testing method, starts with a fresh cut sample to allow precise directional measurement. Then the acoustical velocity is measured relative to a certain locally preferred solidification direction. Following this, the method continues with another fresh cut sample. The acoustical velocity is measured relative to another preferred solidification direction. When the directional acoustical velocities have been recorded, the elastic stiffness matrix can be obtained by the Christoffel equation. Details of these procedures can be found in the study of Dewey et al.

Because the grain growth in the weld nugget is in the [100] direction in the core region, the behaviors of the acoustic waves can be anticipated. However, in other regions of the weld nugget, the microstructures of equiaxed grain growth make the prediction of acoustic wave behaviors difficult. Due to the irregular shape of the nugget, the microstructures in non-core regions of the weld nuggets are equiaxed yet randomly arranged. This affects the pattern of acoustic wave propagation, for example, by misguiding the acoustic waves and return bias signals. The other major factor affecting acoustic wave propagation is the HAZ of the weld. The HAZ has usually been recrystallized and its microstructures have been changed, which results in a re-focusing of the acoustic beam and therefore misinterpretation. Furthermore, the melted coating material will produce contact between the base metals and allow the acoustic waves to pass through. This may change the results of the analysis of the weld nuggets. In some cases, a deep indentation of weld nuggets can re-focus the acoustic beam and produce signal-free regions.

The irregular shape of the nugget raises an interpretation problem for the acoustic method mathematically. An experimental model to predict spot weld quality based on its acoustic information is to be established. By correlating the acoustic parameters and the results from experiments, a reliable index of weld quality can be established.

The results of acoustic image analysis are sets of pixel-based pictures with abundant information that allows us to scrutinize the detail of every aspect of the metallurgical and acoustic properties of each spot weld in the study. The acoustic microscopy method can provide the information about quality of spot weld nuggets by examining the non-homogeneous objects inside nuggets such as: bubbles, inclusions, explosive welds, and porosity. The non-homogeneous objects inside, and the surface indentation, guide the acoustic waves and provide a pseudo-acoustic-image for welded nuggets.

There are two different types of studies performed for the validity test of the acoustic method. The first one is to verify the results of the acoustic method by using another non-destructive method. The second one is to test the ability of the acoustic method by describing the detection of artifact defects. In the first test, the commonly used optical examination procedure is employed as the tool for verifying the result of the acoustic test. The advantages of an acoustic test is that it permits internal examination of structure, but has the disadvantage that the measurement results need to be calibrated. The optical test has the advantage that it allows visual inspection of nugget size but only surface information is obtained.

This approach is aimed at the calibration between the optical method and the acoustic microscope method. Instead of peeling the spot weld samples, this approach works on "peeling nuggets." The procedures of this approach will be described as follows:

1. Cut and grind the welding coupons to nugget tablets.
2. Polish these samples from a selected side.
3. Perform acoustic inspection of spot weld samples from both sides.
4. Examine the peeled nuggets from the selected side by the optical method. Examine the peeled nugget from both sides by the acoustic method. The acoustic signal windows should be set close to the selected side of the nugget. This step will help to examine the correlation between the acoustic method and the optical method.
5. Peel the nugget into thinner tables, and repeat steps 2 through 4.
6. Continue peeling the nugget until the desired thickness has been reached.
7. Calibrate the results from the optical method and the acoustic microscope method.

Verification Results of the Non-Destructive Method.

Three types of welds, categorized by their stack up, were examined to verify results: Type 1 (0.03" stack on 0.045"), Type 2 (0.04" stack on 0.06") and Type 3 (0.06" stack on 0.07"). Two welds of different welding parameters were produced on Type 1, and two and four welds on Types 2 and 3, respectively. For Type 1 and Type 2, the acoustic estimation of the nugget diameter typically closely approximates the diameter determined by the optical method. For Type 3, with thicker base metals which need a longer heating process during welding, the HAZ region is larger than Type 1 and 2. The HAZ affects the microstructures while recrystallization substantially affects both non-destructive tests. For optical examination, the HAZ reacts to the etching process, and produces larger images. In comparison, a ring-shaped region is observed by the acoustic method.

Acoustic Image Study

Figure 7:
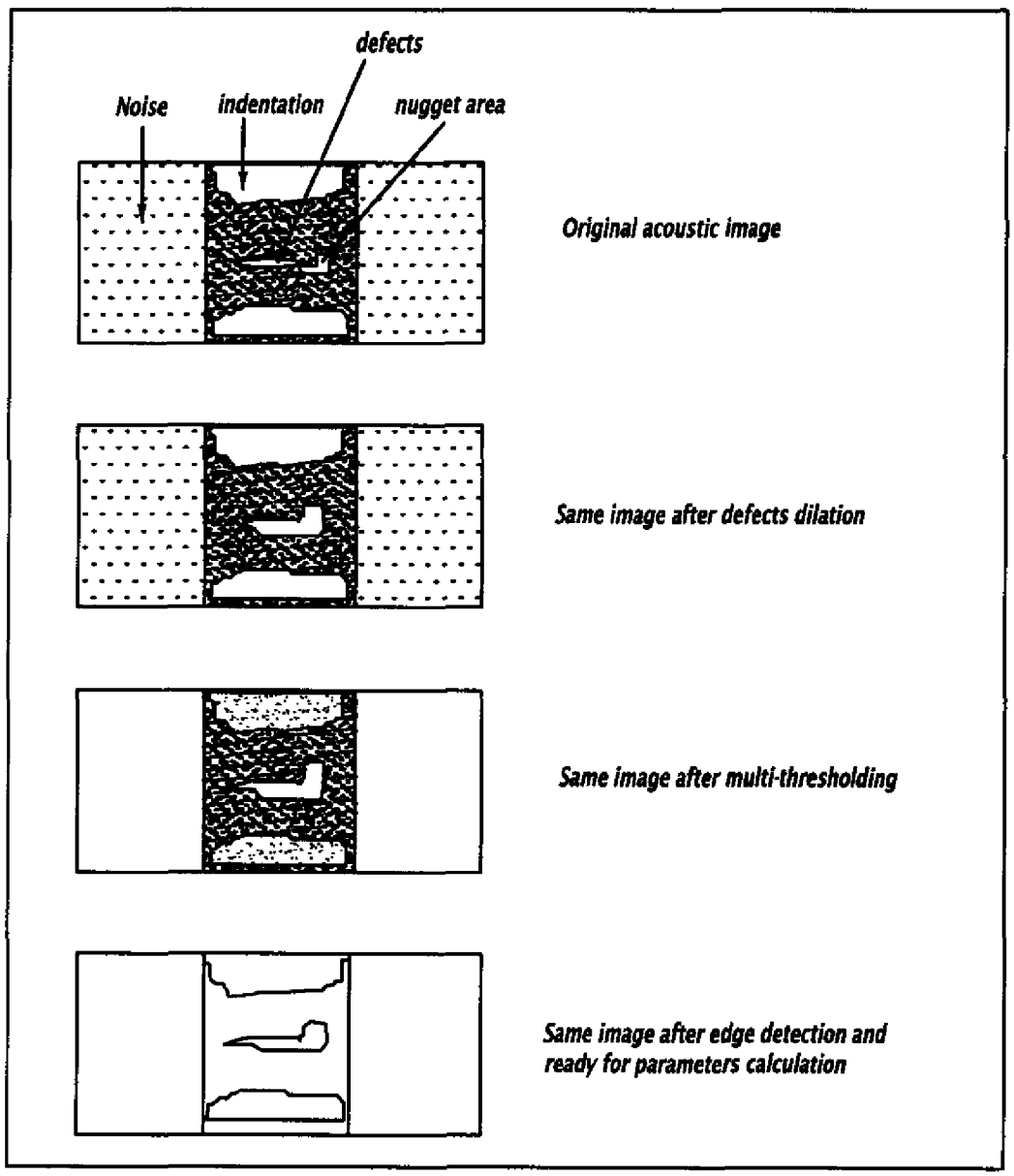
FIG. 7 is a graphical representation of the steps of a method of analyzing and qualifying spot weld joints in accordance with a preferred embodiment of the present invention.

With reference to FIG. 7, to study the acoustic image, four practical steps are employed to convert the information into quantities for further studies. First, mathematical morphology is used to characterize geometric structure by numerical value. This method is usually used prior to image recognition and pattern identification to improve the geometric shapes of objects inside an image for further study. The purpose of the process is to filter out information not related to objects.

The operations of morphology are dilation, erosion, opening and closing. The effect of the dilation operator on an image is to enlarge the boundaries of selected objects. The effect of the erosion operator on an image is to erode the boundaries of selected objects. The opening operation includes performing erosion followed by dilation. The closing operation includes performing dilation followed by erosion. Dilation and erosion operators are used to emphasize the discontinuities inside nuggets. The definition of dilation and erosion operations and their mathematical representation is listed in FIG. 8.

After the acoustic images have been readied for further examination by morphological processes, the thresholding method is used to separate out the interesting objects inside welds, such as weld nugget size, nugget shape, porosity, and inclusion. This algorithm converts a multi-gray-level image into an image containing fewer gray-level values. The operation defined for three gray-level regions for separating noise of image, nugget area, and discontinuities inside nuggets is:

$$g(x, y) = \begin{cases} G_2 & \text{if } f(x, y) > T_2 \\ G_1 & \text{if } T_1 \le f(x, y) < T_2 \\ G_0 & \text{if } f(x, y) \le T_1 \end{cases}$$

where f(x,y) represents the original image; g(x,y) is the image after thresholding; $T_1$ and $T_2$ are thresholding values; and $G_0$, $G_1$ and $G_2$ are the values of gray-level.

After thresholding, edge detection is performed. This process helps separate objects in acoustic images. The edges of objects are distinguished by the discontinuities or abrupt changes in gray-level intensities. Since the gray-level numbers have already been reduced during thresholding, the edges between objects inside the weld nugget are quite clear.

Several other data processing techniques can be used to further enhance the ultrasonic images. These techniques include usage of weighted calculations for ultrasonic signal processing, tilt compensation, surface peak calibration, and time-of flight compensation.

Usage of weighted calculations allows distinguishing poor measurement conditions from good ones. For example, when the transducer is not in a contact with the sample or the surface condition does not allow getting correct measurements, the algorithm will indicate that the measurement is impossible. While standard methods would normally produce a result in any case, it would appear completely inconsistent with reality. For example, in the case of a spot weld, this could lead to the erroneous detection of a normal weld when the weld is in fact undersized.

This functionality is achieved with weights, which specify the degree of reliability of the data. Critical data items are accompanied with this additional weight parameter. Ranging from 0 up to 100%, it specifies the degree of reliability of the data stored in a corresponding item. There are several stages in the data processing pipeline that might change the weight(s) associated with the processed data; mainly weights associated with different transducer elements (different A-scans) are updated during the surface peak detection, based on its signal-to-noise ratio. If the surface peak is indistinct (its amplitude is close to the noise level), the algorithm may reject the channel from further consideration by attributing zero to the corresponding weight. On the contrary, peaks with normal amplitudes are subjected to following data processing stages with 100% weights. A-scans having indistinct peaks are marked with intermediate weight values ranging from 0% up to 100%.

In the case of the spot-weld measurement, interpretation of the final result (the nugget diameter) is quite straightforward. For example, if it has 95% weight, it means that the measurement is likely to be consistent; on the contrary, the low weight of the final result would indicate that the device most likely could not measure the nugget size and the operator has to repeat the measurement.

The tilt compensation method reduces the angular dependence for small, unfocused elements of the matrix transducer. After the algorithm has found the positions and amplitudes of the surface peaks, it measures a global tilt of the surface sample with respect to the transducer surface, which is approximated as a plane. This is done with weighted bilinear regression. Using the empiric tilt-amplitude calibration curve, it computes a factor to compensate the amplitude drop due to the tilt. The value of each sample point in each A-scan is multiplied by that factor. This calibration factor is a global value, and is applied for all transducer channels. This allows receiving C-scans with more stable amplitudes that are less dependent on the transducer tilt. The calibration curve is built as a result of a series of measurements on flat-parallel sheets of metal, mapping the amplitude of the signal received from the back face of the sheet.

Surface Peak Amplitude Calibration is a calibration method that works under assumption that a sample consists of a uniform material. For each transducer channel, it calculates an amplitude multiplication factor that depends on the amplitude of the surface peak. The factor is calculated so that after multiplication, the amplitude of surface peaks are the same for all channels. This calibration method partially compensates for variations of amplitudes due to local surface conditions (i.e., topology variations).

Time-of-Flight (TOF) Compensation is useful since, due to a large difference in the velocity of sound in immersion and in steel, direct mapping of the time axis of an A-scan into the depth is impossible. The sound travels through immersion much slower than it does in metal, and each small variation in immersion thickness causes sufficient displacement of the following signals along the time axis. TOF compensation involves shifting each A-scan along its time axis so that the position of surface peaks becomes the same for all channels. This ensures that the C-scan is acquired from the specified depth range relative to the surface. An analogous effect may be achieved by varying the signal gates position according to the surface peak position. The TOF compensation method stabilizes the range of depths from which the signal is acquired.

Data Analysis

Analysis Method I: Statistical Correlation.

The acoustic imaging method provides abundant information after image extraction. However, this information consumes a major part of the processing resource and is computationally exhausting. Thus it is desirable to limit the parameters that will be used in determining weld quality. In a preferred embodiment of the present invention, the parameters used include nugget diameter, depth of indentation, and area of reflectors inside nuggets. The ideal quality identifier is the strength of the weld nuggets. Quantity is difficult to measure and will vary from process to process. Consequently, a substitute quantity—the diameter measured from the destructive test (peel test)—is used for analyzing the welding quality.

These quantity factors are determined as follows. First a group of selected welding coupons is chosen. Next, a B-scan and C-scan images from the newly developed acoustic device is captured. A group of parameters is selected according to existing knowledge. Destructive tests are conducted on these samples. The nugget diameters of the peel test result are then measured. The ANOVA technique is used to screen out the insignificant parameters. Finally, the nugget strength indicator is built up by correlating significant parameters to the nugget diameters produced by peel tests.

For a three variable system, $\alpha$, $\beta$, and $\gamma$ are related to the nugget diameter S. The linear model will be:

$$S = C_1 + C_2\alpha + C_3\beta + C_4\gamma$$

The polynomial model will be:

$$S = C_1 + C_2\alpha + C_3\beta + C_4\gamma + C_5\alpha\beta + C_6\alpha\gamma + C_7\beta\gamma + C_8\beta^2 + C_9\beta^2 + C_{10}\gamma^{20}$$

where $C_i$, $i=1\sim10$ are constant coefficients.

After the formulation, an ANOVA table can be established to investigate the significance of these variables. Thus, some of the insignificant parameters can be filtered out. The ANOVA provides the inferential procedure for testing the statistical hypothesis. One of the ways to judge the significance of each variable is by assessing the character of the F-score. A level of confidence for the significance test can be set, for example, as either 95% or 99% to select the variables which are to enter the next stage.

Either the linear multiple regression or the non-linear multiple regression method is then used to establish the constants associated with the acoustic parameters. A variety of commercial software exists for solving non-linear regression. Most of them follow this procedure: an initial estimation for each variable is made and a curve defined by the estimation is generated; the variables adjusted to fit the curve closer to data points using algorithms such as the Marquardt method; the curve is further adjusted to make it closer to the data set. Once the pre-set error limit is reached, the procedure is stopped and results are reported.

Through these procedures, a set of significant parameters are determined and their coefficients found. Consequently, the diameter of the weld will be predictable through the cumulative relationship, which will be an indicator of the spot weld quality.

Analysis Method II: Neural Networks.

To assess a spot weld by a general description such as a good/marginal/bad weld (instead of a more specific index, like bonding strength) an artificial neural network (ANN) is used. This general description is desirable as a criterion that can be easily adopted into industrial standards.

Figure 9:
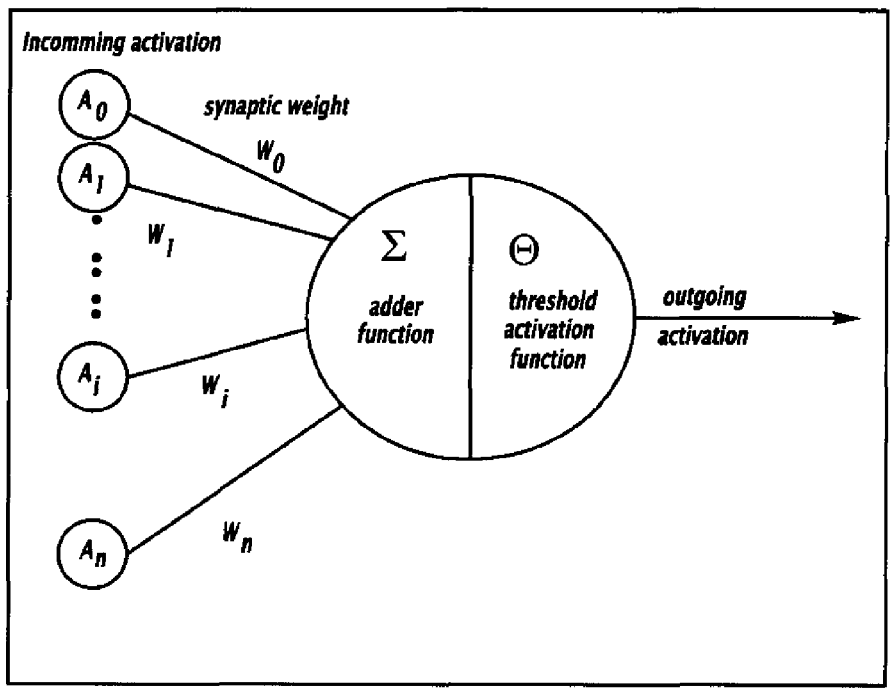
FIG. 9 is an abstract model of a neuron.

ANN were originally designed as a model to simulate how the human brain works. With reference to FIG. 9, the ANN is a simplified model that simulates human information passing behavior by artificial neurons. Each neuron has input and output which are related to the state of the neuron itself, a threshold function to decide on the input-output relationship, and unidirectional connection communication channels which carry numeric (as opposed to symbolic) data.

Figure 10:
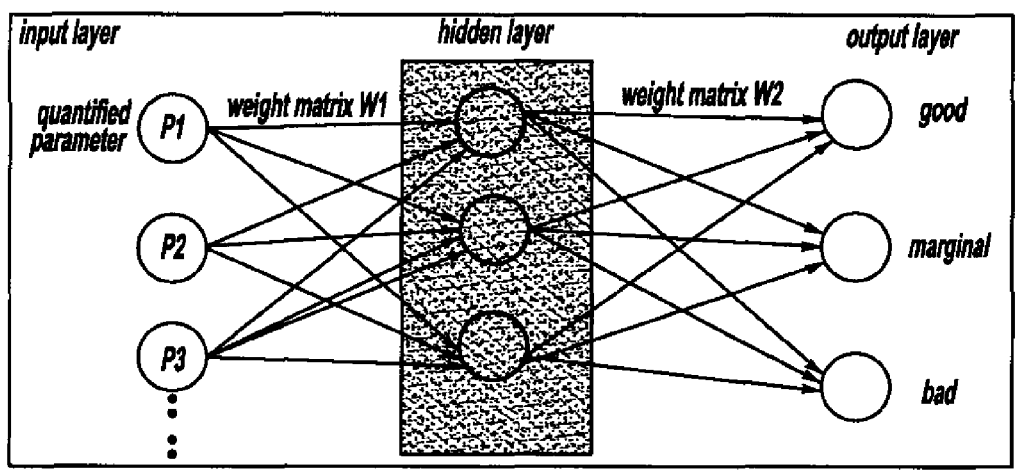
FIG. 10 is a multi-layer feed-forward neural network in accordance with a preferred embodiment of the present invention.

With reference to FIG. 10, the neural network model of the present invention is a three layer feed-forward model trained with the back propagation method with logistic function as the activation function. The logistic threshold function is:

$$f(x) = \frac{1}{1 + e^{-x}}$$

where $f(x)$ represents the output; and x is the input.

The back propagation method is desirable because it is easy to apply to a practical problem such as the problem examined. This algorithm has been proven as very robust for training multiple layer networks. It is also desirable because it is very effective when the relationship between input/output layers is nonlinear and the training data is abundant.

According to a preferred embodiment of the present invention, there are i quantified parameters, j hidden units, and three output units (representing good/marginal/bad welds). $W_{ij}$ stands for the weight between input layer i-th unit and j-th unit of the hidden layer. The activation function here has a special property such that $f(x)=f(x)(1-f(x))$. The steps of the back propagation method of the present invention include:

1. Computing the hidden layer neuron activation. The j-th hidden layer neural:

$y_j = f((\Sigma_i x_i W_1[i|j]) + \theta_j)$

2. Computing the output layer neuron activation. The j-th output layer neural:

$z_j = f((\Sigma y_1 W_2[i|j]) + \tau_j)$

3. Computing the output layer error, where the output differences are equal to the desired values minus the computed values. For the i-th component of error at the output layer:

$e_i = z_1(1-z_1)(p_1-z_1)$

4. Computing the hidden layer error. For the i-th component of error at the hidden layer:

$t_1 = y_1(1-y_1)(\Sigma_j W_2[i|j] e_j)$

5. Adjusting the weights for the second layer of the synapses. For the i-th neuron in the hidden layer and the j-th neuron in the output layer:

$\Delta W_2[i|j] = \mu y_i e_j$

6. Adjusting the weights for the first layer of the synapses. For the i-th neuron in the input layer and the j-th neuron in the hidden layer:

$W_1[i|j] = \lambda x_i t_j$

Steps 1 though 6 are then repeated on successive training data until a specified value of output layer error is achieved. In the above described back propagation equations, x, y, z are vectors for the output neurons in the input layer, hidden layer, and output layer, respectively; $W_1$ and $W_2$ are weight matrices between the input-hidden layer and the hidden/output layer; p is the desired output vector; $\Theta$ and t are vectors for errors in the output and hidden layers; $\theta$ and $\tau$ are vectors of the threshold or bias value for the hidden layer and the output layer; and $\mu$ and $\lambda$ are learning rate parameters for the hidden layer and the output layer.

The back propagation network has the ability to learn any arbitrarily complex nonlinear mapping. With respect to the statistics method, the proposed feed-forward method with one hidden layer is a very close projection pursuit regression.

In the preferred embodiment of the present invention, the software acts as an analyzer with image processing tools. It performs neural network training and testing functions. Users can load images, perform basic image processing techniques, run default operations (thresholding/dilation/area calculation), prepare ANN training data, train ANN, prepare testing data, and test ANN results. In another mode of operation, the software, the software performs spot weld quality examination on pre-trained ANN.

EXAMPLES

The above system and methods will now be illustrated with several examples. These examples include examined specimens produced under carefully controlled welding parameters (welding current, electrode pressure, and holding time) and identical metal conditions (e.g., surface coating, thickness). Due to the continuous hardware improvement, weld specimens were separated into three groups chronologically. The first group, with C-scan images as the results, was examined earlier by ultra-Short Pulse Scanning reflection Acoustic Microscope (SPSAM). The quality of these specimens was certified by experts from the best to the worst as setup, nominal, minimum, less than minimum, and stick weld, respectively. The minimum quality is the bottom line of an accepted weld. The second group, with C-scan images as the results, was examined by SPSAM as well. This group was peel tested and served as the verification group to test the Artificial Neural networks (ANN) model built by Group One. The specimens of Group Three were examined by both the portable hand-held microscope and SPSAM.

Non-destructive acoustic tests were applied to specimens and acoustic information was recorded. Then destructive testing was conducted on the second and third groups of specimens for conventional nugget diameter measurement. Through destructive tests, the nugget size of each spot weld was found. This information was then integrated into the results together with the parameters recognized by a method described below. The experimental procedures for the specimens are listed in FIG. 11.

Example Group One

Two types of metal stack up were studied: Type I (0.03"×0.045") and Type II (0.04"×0.06"). The criteria for identifying weld quality by experts for each metal stack up is based on the size of the weld nugget. The criteria are listed in FIG. 12.

FIG. 13 lists exemplary results obtained by the acoustic image measurement and analysis methods detailed above. These results involve the quality indicator (e.g., setup, nominal, minimum, less than minimum, stick) and will be adopted in the ANN model developed for this study. Among these specimens, 120 samples including 24 setup, 24 nominal, 24 minimum, 24 less than minimum, and 24 stick were chosen for each type of stack up to train the ANN. The other 75 samples for each type were used to test the neural networks model. In Type I stack up, all 75 samples match the actual weld quality of the ANN corresponding model. For the Type II stack up, 71 out of 75 samples match the weld quality of the corresponding ANN model. The results indicate a coherent performance for this model based on expert knowledge.

Figure 14:
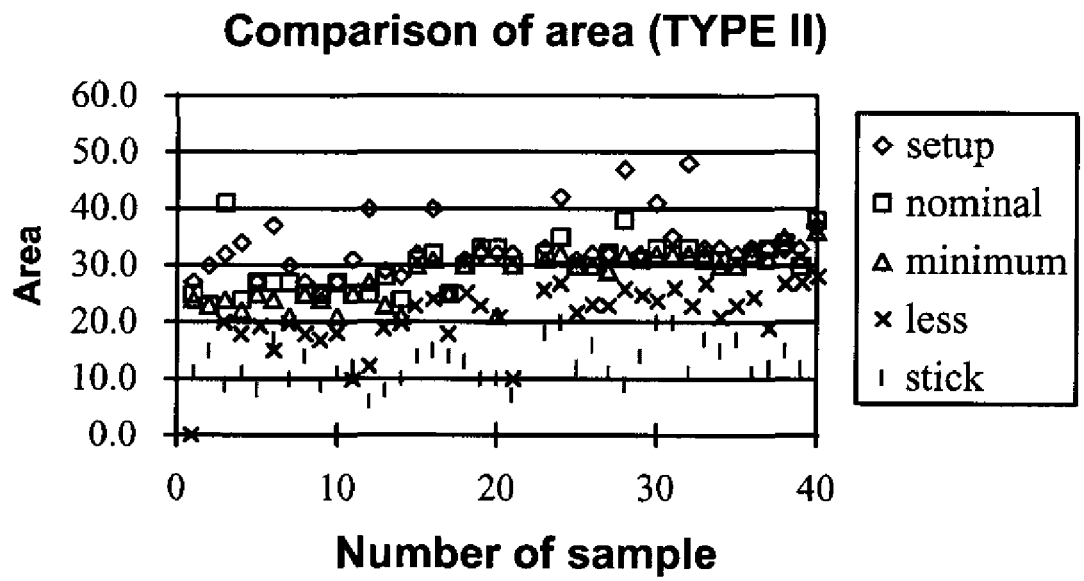
FIGS. 14-16 are graphical representations of exemplary experimental results in accordance with a preferred embodiment of the present invention.
Figure 15:
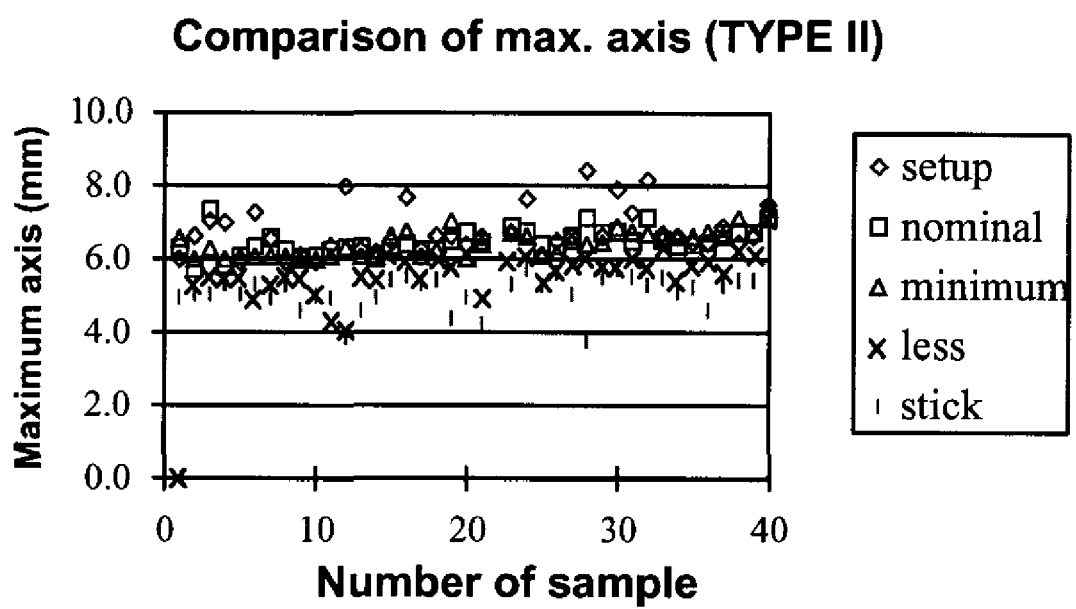
Figure 16:
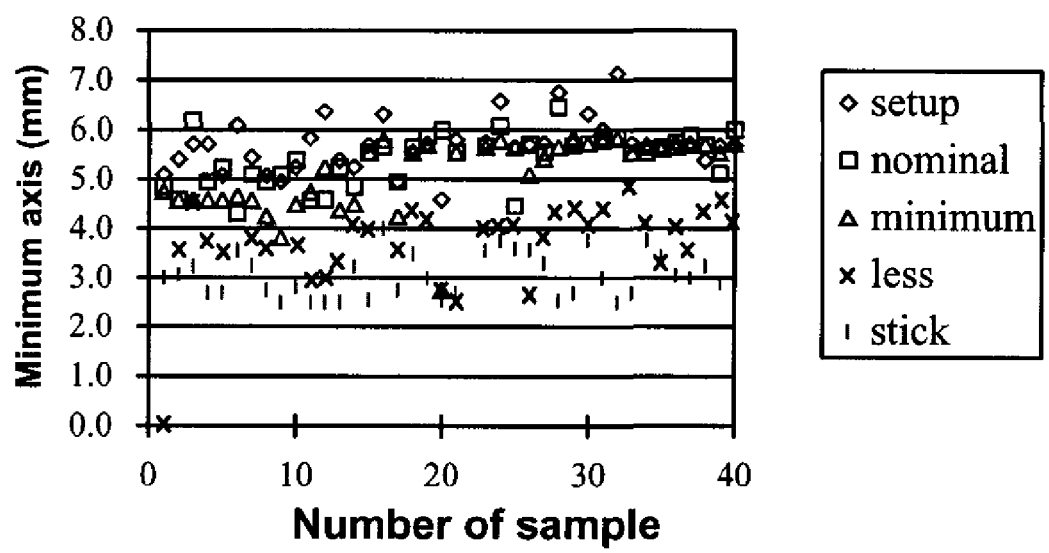

The results of Type II are plotted in FIGS. 14-16 according to the selected acoustic parameters (area, maximum nugget diameter, and minimum nugget diameter). There exists no clear boundary between weld quality by considering a single parameter. For example, in FIG. 14, the range of "minimum" quality and "less than minimum" quality are overlapped between 20 and 30. In other words, the quality of weld cannot be decided by a single acoustic parameter.

Example Group Two

The following set of examples include one type of metal stack up (Type I, 0.03"×0.045"). This group of specimens is acoustically examined and peel tested. The acoustic C-scan images are used to test the corresponding ANN model built by the specimens of Group One. The verification is 100% consistent to both (peel test and ANN) models. The results are listed in FIG. 17.

Example Group Three

Figure 19:
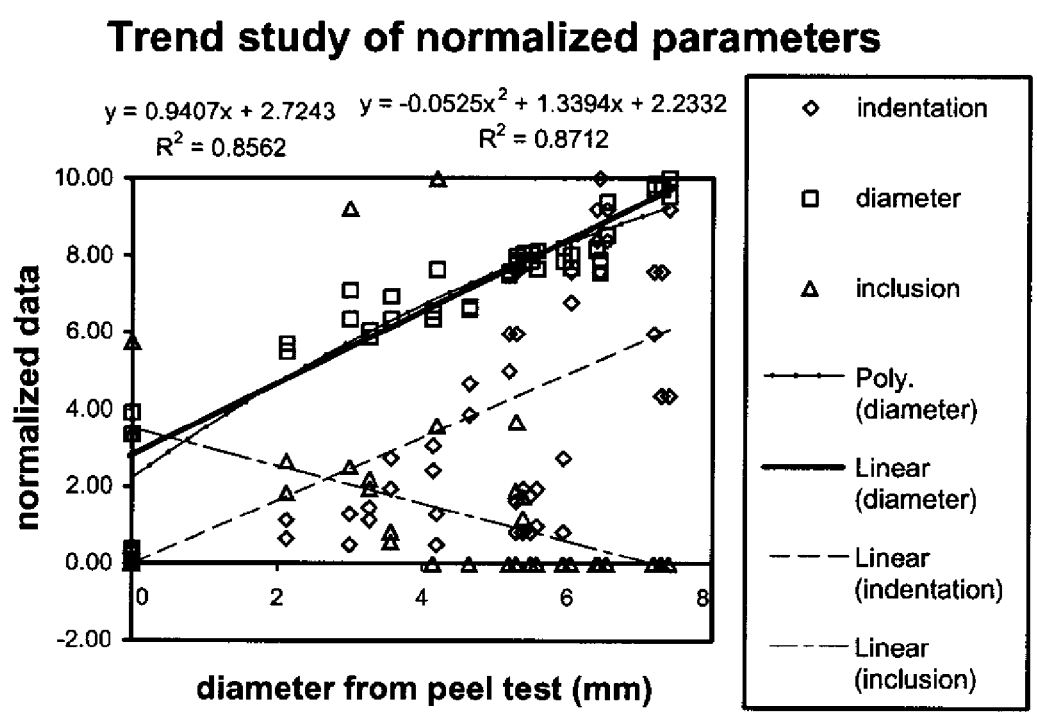
FIG. 19 is a graphical representation of exemplary experimental results in accordance with a preferred embodiment of the present invention.

In this set of examples, the three parameters chosen for analyzing the weld quality are surface indentation, nugget diameter (measured from the acoustic method), and the total inclusion size inside the nugget. The data of these parameters and the results from the peel test are included in FIG. 18. The experimental result is normalized and plotted in FIG. 19 to provide visual assistance for choosing a proper interpretation of the weld quality.

There is no significant relationship between the normalized data and the diameter measured from the peel test. The only parameter capable of portraying the relationship is the distance between the weld boundaries, the order of which cannot be decided since the coefficient of determination of the first and second order equations are so close. Therefore, both linear and nonlinear regression models are tested for determining the suitable model. The appropriate model is then used to carry out the magnitude of the coefficients of the equation.

These three variable systems, $\alpha$, $\beta$, and $\gamma$, which represent indentation, acoustic diameter, and inclusion, respectively, are related to the diameter from peel test D. The linear model is:

$$D=C_0+C_1\alpha+C_2\beta+C_3\gamma$$

The polynomial model is:

$$D=C_0+C_1\alpha+C_2\beta+C_3\gamma+C_4\alpha^2+C_5\beta^2+C_6\gamma^2+C_7\alpha\beta+C_8\beta\gamma+C_9\alpha\gamma$$

where $C_i$, $i=0\sim9$ are constant coefficients.

Figure 22:
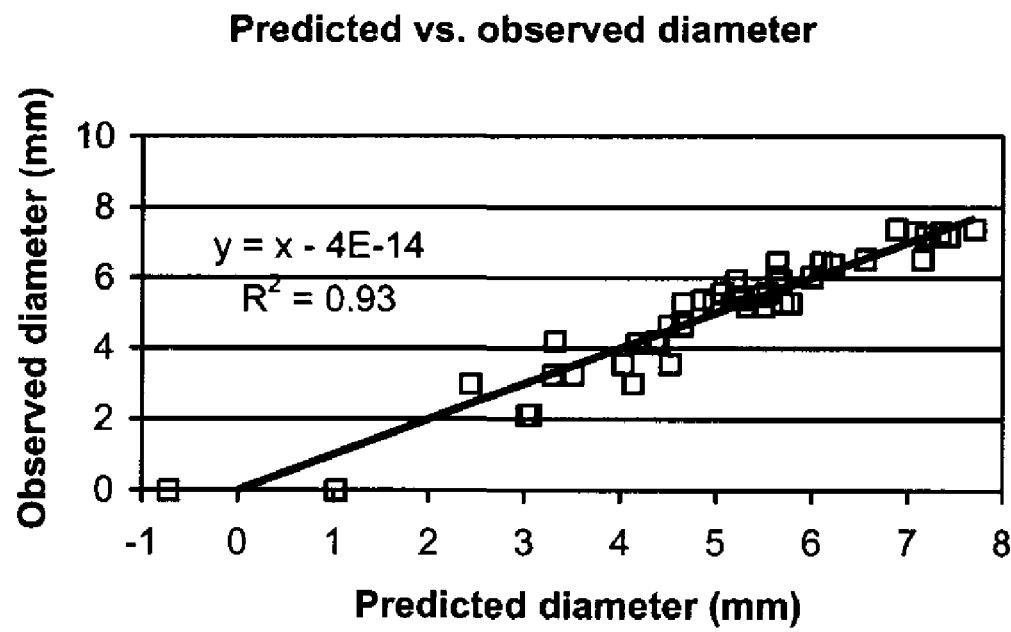
FIGS. 22 and 23 are graphical representations of exemplary experimental results in accordance with a preferred embodiment of the present invention.
Figure 23:
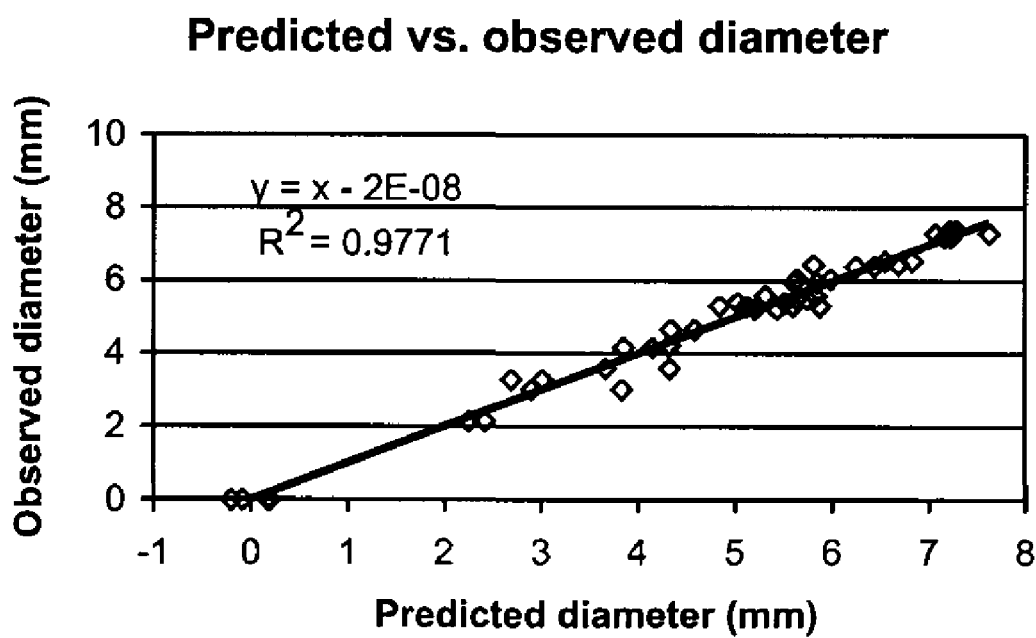

The coefficients of the linear and nonlinear regression models are shown in FIG. 20, and the results are plotted in FIG. 22 and FIG. 23, respectively. FIG. 23 demonstrates that the polynomial model with ten (10) constants is a closer prediction. The F-score of this model is 170.36, which is substantially greater than the F-critical value of 2.17. Therefore, this regression model is useful in predicting the diameters measured by the peel test. The sum of the residual square is reasonably small at 4.28.

To reduce the calculation efforts of this model, a t-test for the statistical significance of each parameter is performed. The significance level is chosen as 95%, and the t-value is 1.645, which suggests that some of the terms are insignificant. Hence the reduced equation can be rewritten as:

$$D=C_0+C_1\alpha+C_2\beta+C_3\alpha^2+C_4\beta^2+C_5\gamma^2+C_6\alpha\beta$$

The coefficients are listed in FIG. 21.

The new model provides an explanation without losing much of the generality of the observed diameter with the coefficient of determination equal to 0.969. The sum of the residual square is 5.755.

Through these procedures, a set of significant parameters is determined their coefficients are retrieved. The peel diameter of the weld will be predictable through the cumulative relationship, which will be an indicator of spot weld quality.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of analyzing an ultrasound image, the method comprising the steps of:
    identifying critical data items in the ultrasound image;
    assigning each critical data item a weight parameter specifying the reliability of the data stored in a corresponding data item;
    performing surface peak detection on the ultrasound image;
    altering a weight parameter for a data item based on the results of the surface peak detection to reflect a change in reliability;
    accepting and rejecting data items based on their respective weight parameters; and
    displaying accepted data items.

2. The method of claim 1, wherein the data items represent ultrasound transducer channels.

3. The method of claim 2, further comprising the step of rejecting a channel from further consideration based on the corresponding weight parameter.

4. A method of analyzing an A-scan ultrasound image to reduce the angular dependence of matrix transducer elements and improve C-scan image quality, wherein the ultrasound image represents a surface sample of a spot-weld joint, the method of comprising the steps of:
    locating the positions and amplitudes of surface peaks in the ultrasound image;
    measuring a global tilt of the surface sample with respect to the transducer surface, using weighted bilinear regression;
    using an empiric tilt-amplitude calibration curve to compute an amplitude drop compensation factor based on the global tilt; and
    multiplying the value of each sample point in each A-scan by the amplitude drop compensation factor, such that the factor is applied for all transducer channels;
    wherein subsequently acquired C-scan images have more stable amplitudes that are less dependent on the transducer tilt than images acquired using un-compensated transducers.

5. The method of claim 4, further comprising the step of building the calibration curve, wherein building the curve includes the steps of:
    using a series of measurements on flat-parallel sheets of metal; and
    mapping the amplitude of the signal received from the back face of the sheet.

6. A method of compensating for variations in the velocity of sound in different media in the analysis of ultrasound images, wherein an ultrasound transducer system is used to acquire ultrasound images, the method comprising the steps of:
    acquiring a set of A-scan ultrasound images;
    shifting each A-scan along its time axis so that the position of surface peaks for becomes the same for all ultrasound transducer channels;
    building a C-scan image from the A-scan images, wherein the C-scan image reflects the shifting; and
    displaying the C-scan image.

* * * * *